(12) United States Patent
Liu et al.

(10) Patent No.: US 8,226,559 B2
(45) Date of Patent: Jul. 24, 2012

(54) METHOD AND APPARATUS FOR REAL-TIME TEMPERATURE MEASURING FOR HIGH-INTENSITY FOCUSED ULTRASOUND(HIFU) THERAPY SYSTEM

(75) Inventors: Hao-Li Liu, Tao-Yuan (TW); I-Yeh Lu, Shulin (TW); Sheng-Min Huang, Pingjhen (TW)

(73) Assignee: Chang Gung University, Tao-Yuan (TW)

( * ) Notice: Subject to any disclaimer, the term of this patent is extended or adjusted under 35 U.S.C. 154(b) by 1080 days.

(21) Appl. No.: 12/155,689

(22) Filed: Jun. 9, 2008

(65) Prior Publication Data
US 2009/0182230 A1 Jul. 16, 2009

(30) Foreign Application Priority Data
Jan. 16, 2008 (TW) .............................. 97101598 A (51) Int. Cl.
*A61B 8/00* (2006.01)
*G01N 29/00* (2006.01)
(52) U.S. Cl. ........................ 600/438; 600/439; 73/602
(58) Field of Classification Search ........................ None
See application file for complete search history.

(56) References Cited

OTHER PUBLICATIONS

Vazquez et al. "Noninvasive Temperature Estimation in Oncology Hyperthermia Using Phase Changes in Pulse-Echo Ultrasonic Signals." JP J of Applied Physics. vol. 45, No. 10A, 2006. pp. 7991-7998.*
Simon et al. "Two-Dimensional Temperature Estimation Using Diagnostic Ultrasound." IEEE Trans. on Ultrasonics, Ferroelectrics, and Frequency Control, vol. 45, No. 4, Jul. 1998. pp. 1088-1099.*
Maass-Moreno et al. "Noninvasive temperature estimation in tissue via ultrasound echo-shifts. Part I. Analytical Model." J Acoustical Society of America, vol. 100, No. 4, 1996. pp. 2514-2521.*
Maass-Moreno et al. "Noninvasive temperature estimation in tissue via ultrasound echo-shifts. Part II. In vitro study." J Acoustical Society of America, vol. 100, No. 4, 1996. pp. 2522-2530.*
Seip et al. "Noninvasive Estimation of Tissue Temperature Response to Heating Gields Using Diagnostic Ultrasound." IEEE Transactions on Biomedical Engineering, vol. 42, No. 8, Aug. 1995. pp. 828-839.*
Liu et al. "Instantaneous Frequency-Based Ultrasonic Temperature Estimation During Focused Ultrasound Thermal Therapy." Ultrasound in Medicine & Biology, vol. 35, No. 10, 2009. pp. 1647-1661.*

* cited by examiner

*Primary Examiner* — Long V. Le
*Assistant Examiner* — Angela M Hoffa
(74) *Attorney, Agent, or Firm* — Bacon & Thomas, PLLC (57) ABSTRACT

The invention is disclosed to design a real-time pulse/echo system to perform 1-D real-time temperature measurement and integrate in the high-intensity focused ultrasound system. In the invention, a modified echo-time shifting algorithm is developed to calculate the corresponding phase shift from echo signal, which correlates with the instantaneous temperature change during heating process.

3 Claims, 12 Drawing Sheets

METHOD AND APPARATUS FOR REAL-TIME TEMPERATURE MEASURING FOR HIGH-INTENSITY FOCUSED ULTRASOUND(HIFU) THERAPY SYSTEM

BACKGROUND OF THE INVENTION

1. Field of the Invention

The present invention relates to a real-time temperature measuring, and more particularly, to an apparatus for real-time temperature measuring by using the ultrasound system.

2. Description of the Prior Art

In the clinical therapy at recent years, the High-intensity focused ultrasound thermal (HIFU) therapy has already been paid highly attention, wherein the thermal therapy is a kind of non-invasive therapy way which is used in the control of cancer cell and tissue burn etc. Thus the non-invasive therapy has become the biggest feature of ultrasound therapy, and it is unable to be replaced in the medical treatment.

During HIFU treatments, temperature monitoring for treatment guidance is essential for control and treatment optimization. Among the medical imaging modalities, magnetic resonance imaging (MRI) has been proven to precisely detect temperature changes during a treatment due to the effect of temperature-dependent proton resonance frequency shifts.

In the thermal therapy process, in order to control the degree of heating to avoid injuring the normal cell tissue of the surrounding area, the real-time temperature measuring system having the instantaneous regional temperature change is very important. If there is no such kind of monitoring heating system, the clinical doctor is unable to grasp the detailed temperature change accurately in the body. Not only the difficulty of therapy and the danger of operation will be increased, but also the clinical application of thermal therapy will be restricted greatly.

However, in order to use MRI for temperature monitoring, the HIFU system must be designed to be magnetic-resonance compatible, which largely increases the complexity of the system design and increases the cost for its use in clinical applications. Another potential approach to provide sufficient temperature sensitivity and yield good spatial resolution for medical imaging is diagnostic ultrasound. A very basic concept is that the backscattered ultrasound RF echo from the region experiences time shifts after the tissue is heated, which has been identified to be a gross effect including the change in the sound speed and thermal expansion of the tissue in the heated region due to temperature changes. An attractive feature of using diagnostic ultrasound to monitor temperature during HIFU treatments is that this technique is relatively less expensive, portable, and can be easily employed in almost any current HIFU systems with little concern about system compatibility.

Among the ultrasound-based temperature estimation techniques, both frequency-domain-and time-domain-based processing schemes have been proposed. In the prior art, a spectral processing technique was used. The temperature change estimation along one dimension was achieved by tracking the frequency variation in the echo components in the spectral domain; the echo spectrum was estimated using an autoregressive (AR) model. However, the difficulty in implementing this algorithm involves the selection of the order of the AR model and the necessity to have two or more scattering centers per window. As compared to spectral-based processing schemes, a major advantage of time-domain processing is computational efficiency. Moreno et al. and Simon et al proposed that time-domain signal processing schemes are feasible for temperature estimation, where these techniques are conceptually identical to blood flow estimation using pulsed Doppler system.

By using classical quadrature demodulation, the phase differences in successive echoes from moving targets are detected, and the phase change in the signal can be estimated and accumulated; resultantly, the temperature information can be extracted. Although there is an improvement in the computational efficiency, the computation of cross-correlation still involves extensive processing, hindering the progress of the real-time implementation of temperature estimation.

At present, the relevant measuring known in the prior art include the human resistant temperature measuring method, magnetic resonance imaging measuring method, infrared temperature measuring method and ultrasound tissue temperature measuring method etc. These techniques can be used to monitor the tissue temperature, but each technique has its own shortcomings. For example, the shortcomings of the human resistant temperature measuring method are poor space resolution and higher variation, and it is seldom used in the clinical application. Though the magnetic resonance imaging measuring method can provide higher space resolution, but the real-time measurement is unable to be achieved due to slower scanning speed. Moreover, the procurement cost of equipments will be very high and the volume space of system will be quite huge, and it is not easy to be integrated with other thermal therapy methods, thus it is not practical in the clinical thermal therapy. The infrared temperature measuring method is unable to provide the temperature change of deep tissue, thus it is not suitable to be used as the monitoring equipment of temperature change in the thermal therapy process.

However, the insufficient information for the inside temperature of tissue become the greatest restriction in the process. Though the traditional ultrasound technique can be used to obtain temperature distribution information, but the operating time is too long, and the real-time information is unable to be obtained, thus it is not suitable for the clinical therapy.

Quite clinically, the application of ultrasound as the tool for diagnosing the disease has already been used widely, and its safety has been trusted. The main advantages are the followings: non-invasive measurement, real-time image scanning, strong system mobility, and cheap system cost etc. Thus, if the ultrasound system can be utilized to develop non-invasive temperature monitoring system for the tissue, and can be combined other medical systems such as the ultrasound imaging system, the application range of clinical thermal therapy and relevant medical safety will be able to be increased greatly.

SUMMARY OF THE INVENTION

The present invention relates to an ultrasound temperature measuring technique. It possesses a temperature calculation algorithm to analyze the signal of ultrasound radio frequency (RF). It can eliminate the shortcoming of traditional algorithm in which the real-time temperature information is unable to be obtained.

The components of the invention comprise the followings: ultrasound burning module, real-time temperature monitoring signal treatment module, ultrasound signal interference module, and computer graphics user interface system control program.

The ultrasound burning module of the invention will comprise the followings: signal input source, amplified circuit device and ultrasound probe. It can produce a high-power focused ultrasound to perform burning process.

The signal treatment procedure of the invention comprise the followings: temperature calculation algorithm for the signal of ultrasound radio frequency (RF), design of pre-filter and post-filter is carried out.

The present invention provides a mathematical model theoretically. This mathematical model can shorten the calculation time greatly and achieve real-time purpose compared to the conventional algorithm. If the ultrasound imaging meter is used together, the real-time temperature distribution image can be obtained.

The purpose of the invention is to integrate the ultrasound burn having temperature control system and graphics user interface design to become effective thermal therapy system.

DESCRIPTION OF THE PREFERRED EMBODIMENT

The method of the invention is to use the change of sound speed under different temperature, the echo signal of ultrasound generate the phase shift on time axle, and then reduce the temperature difference to obtain temperature measuring result.

Figure 1:
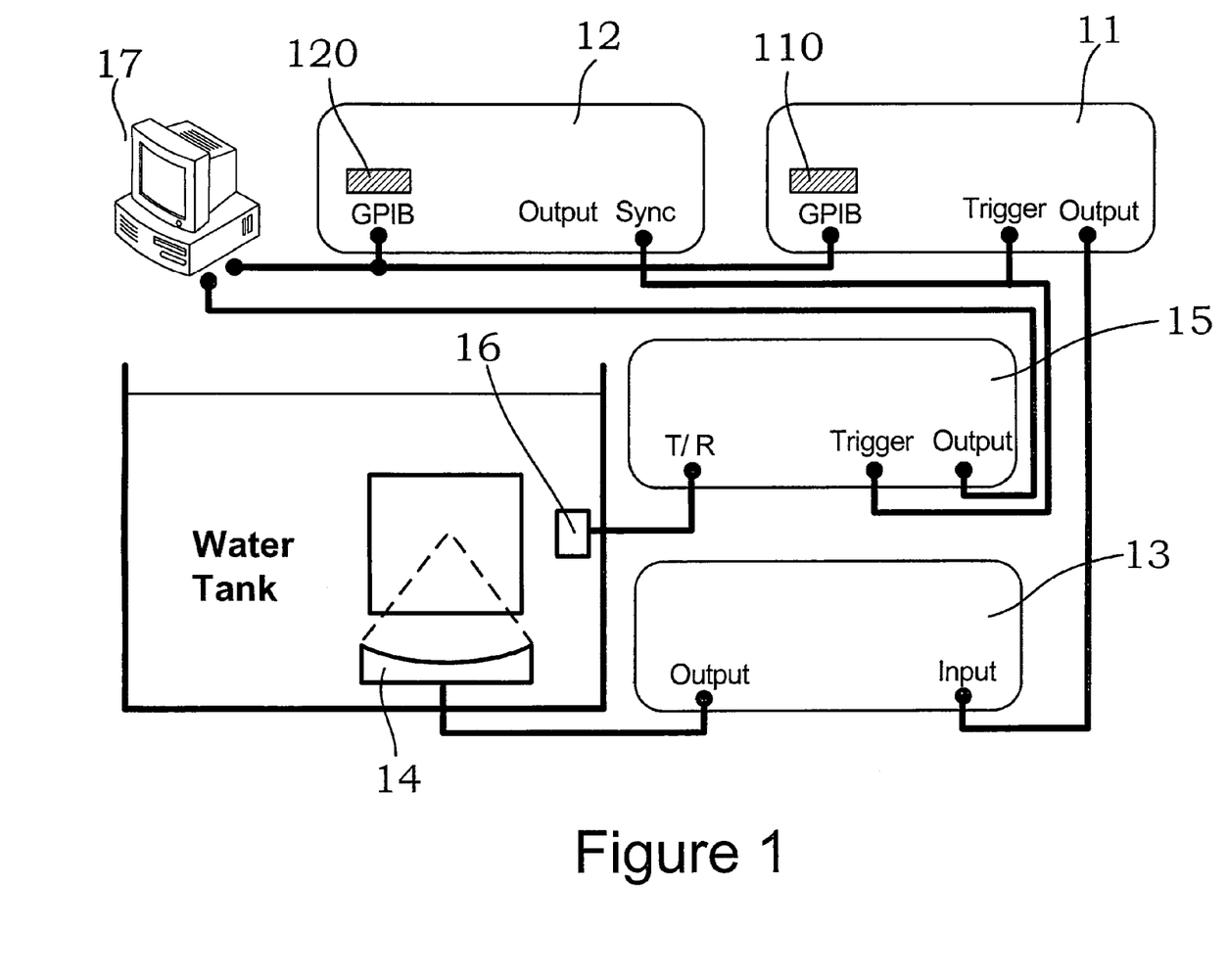
FIG. 1 is the diagram schematically illustrating the complete structure for the system of the invention.

As shown in FIG. 1, the schematic structure for the system of the invention is disclosed. The ultrasound burn module of the invention provides hot burning function, comprising first signal generator 11, power amplifier 13, first focused ultrasound probe (i. e. ultrasound energy transfer device) 14, and probe 14 can be adjusted the focused position and computer 17.

As shown in FIG. 1, the ultrasound signal interference module of the invention is disclosed schematically. The function is to avoid producing heat burn phenomenon. It comprises first signal generator 11, second signal generator 12, pulse generator/receiver 15, and second focused ultrasound probe 16.

As shown in FIG. 1, the real-time temperature monitoring module of the invention comprises pre-filter 110 in the first signal generator 11, a post-filter 120 in the second signal generator 12.

In the heating source module of the invention, the first signal generator 11 generates the working frequency. After the cluster wave is generated by the second signal generator 12, the cluster wave is sent to the power amplifier 13, the output power of ultrasound is adjusted and sent to the first focused ultrasound probe 14 (i. e. the first probe 14), which is focused to become the heating source.

In the temperature measuring module of the invention, the ultrasound pulse generator/receiver 15 is used to drive the second focused ultrasound probe 16 (i. e. the second probe 16) to emit the ultrasound signal. Pass through the focus of the first focused ultrasound probe 14 is passed through in the heating system, which is the heating center. The echo signal of reflected wave is received. The signal intercepting card of computer 17 is used to transform the received ultrasound echo signal into digital signal and store it in computer 17 for analysis.

Figure 2:
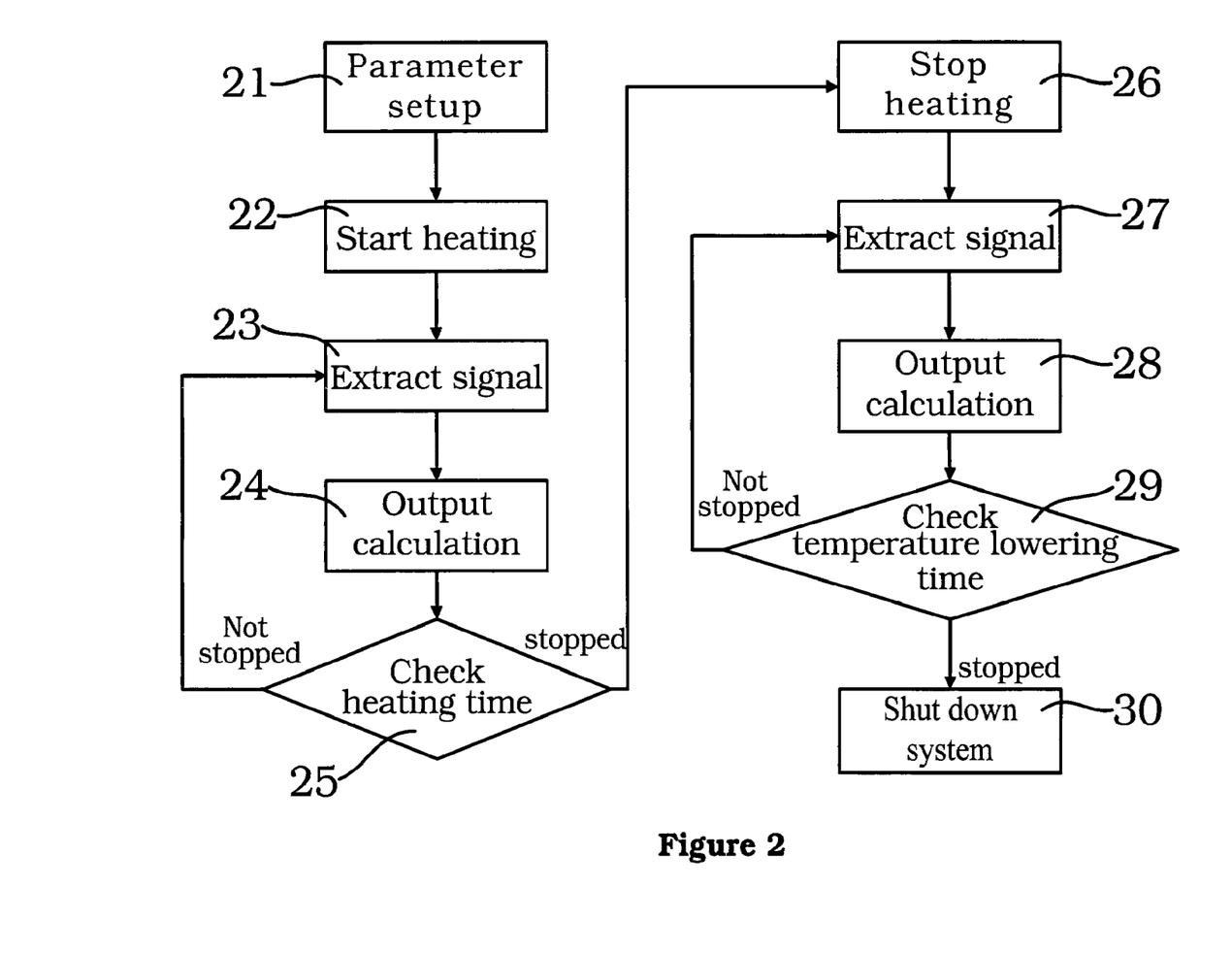
FIG. 2 is the diagram schematically illustrating the flow diagram for process control of the invention.

As shown in FIG. 2, the flow diagram for computer process control of the invention is disclosed schematically. In the invention, the computer is used to integrate the control, and the continuous sine wave is used to drive the first focused ultrasound probe 14 to heat the biological phantom. In order to prevent the serious interference of echo wave due to the interference of signal at the measuring probe, it is necessary to reduce the heating signal in the environment. Thus in the procedure of the invention, after the parameter setup 21 is finished, the heating is started 22. It means after the heating system is activated for 3 seconds, it is shut down for 0.5 seconds for pulse/echo signal acquisition. After the system environment is steady, extract the signal 23. It takes about 0.5 seconds for the measuring system to receive the data. Even this example is given by the preliminary experimental test, though still not fully limited by the preliminary experimental test. Thus, the turn-on duration and switching frequency of the focused ultrasound sonication and pulsed/echo signal acquisition can be arbitrary given.

The calculation result is outputted 24. It is iterated later. The heating time is checked 25. The heating is stepped 26 until total set heating time is up. The heating system will not be activated again. Then, the signal is extracted 27 per 4 seconds, so that the data at the temperature lowering can be recorded. The calculation result is outputted 28. The temperature lowering time is checked 29. Total temperature lowering time shall be 2 times of the heating time. All signals are stored in the computer. Finally, shut down the system 30 is carried out.

When the procedure is over and the biological phantom is recovered to normal temperature, the procedure will be repeated. The ultrasound extracting system is replaced by the thermocouple to compare the result with actual temperature change.

Figure 3:
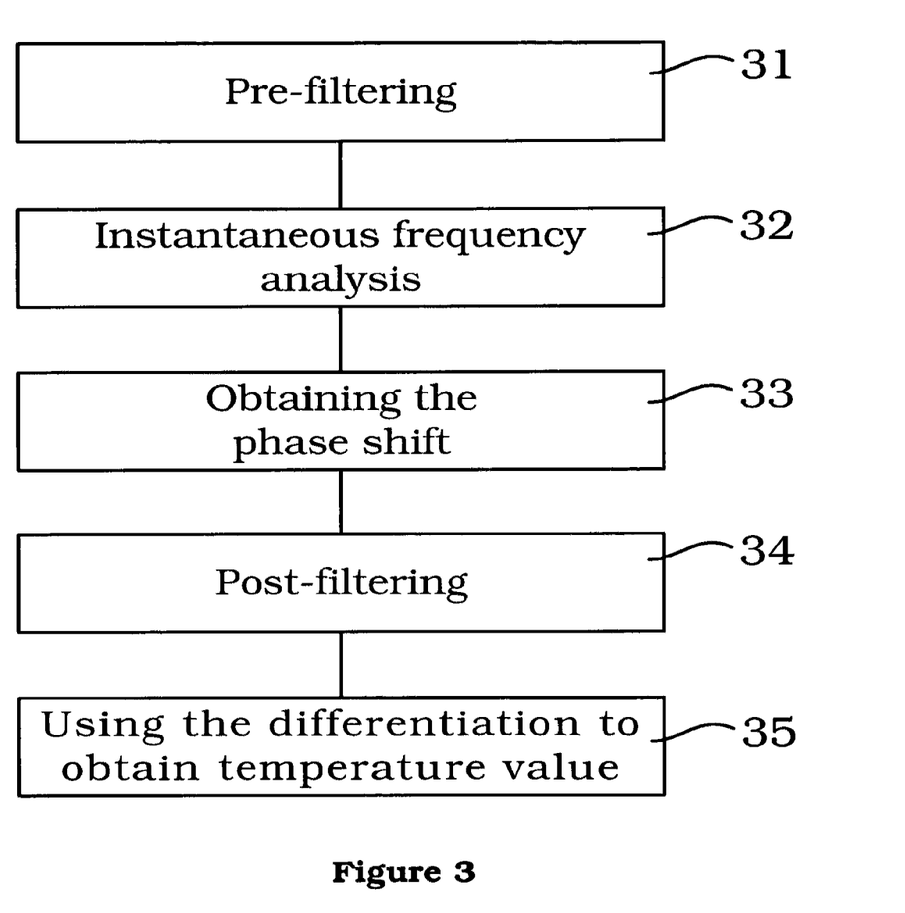
FIG. 3 is the diagram schematically illustrating the flow diagram for signal treatment procedure of the invention.

As shown in FIG. 3, the flow diagram for signal treatment procedure of the invention is disclosed schematically. It shows the ultrasound temperature detection technique and the interference avoiding mechanism of the invention. As for 31 labeled in FIG. 3, the pre-filter is used to filter the first noise signal. Better temperature measurement effect will be obtained. The first wave filtering treatment is conducted for the ultrasonic radio-frequency (RF) in the system, and the purpose is to filter the noise signal caused by the external factor such as vibration in the environment, in order to reduce the error in the analysis procedure. The band pass filter is used. The cutoff frequency is the central frequency of ultrasound probe plus and minus 500 KHz.

Next, as for 32 labeled in FIG. 3, the instantaneous frequency analysis is carried out. The filtered signal is analyzed by the mathematical algorithm to obtain the change instantaneous angular frequency.

Then, as for 33 labeled in FIG. 3, the phase shift is obtained, which is the temperature difference with the reference temperature. Due to the phase shift is influenced by the hot lens effect, thus the performance is not stable at the end part. The phase is not linear accumulation as expected at the relative position after heating point, which causes the oscillation of phase shift.

Subsequently, as for 34 labeled in FIG. 3, the zero phase filter is used to improve the oscillation of phase shift. It means the post-filter is used to filter the second noise signal.

Finally, as for 35 labeled in FIG. 3, the differentiation way is used to obtain temperature value. It means the first derivative of phase shift is obtained to get good temperature measurement.

The mathematical algorithm is used to carry out the relevant calculation in the invention, which means the temperature measuring algorithm of the ultrasound radio frequency signal is used. Firstly, assume the ultrasound echo signal at the initial temperature and the ultrasound echo signal at the changed temperature are shown as followings:

$$S_i(x,t) = A(x,t)\cos(w_0(t)t(x)) \quad (1)$$

$$S_t(x,t) = A(x,t)\cos(w_0(t)t(x) + w_0(t)\delta t(x)) \quad (2)$$

In the invention, as for the ultrasound signal of the same measuring object, when the temperature is changed, the phase shift of echo signal can be regarded as the result for the compression of time-domain signal.

In the other words, when the time-domain signal is compressed, the instantaneous angular frequently will be changed in frequency domain. Thus, the phase shift of time-domain can be regarded as the clockwise shift amount of frequency in the frequency domain.

If equations (1) and (2) are expressed by the complex number, and the imaginary number part is obtained from Hibbert transformation of real number part, the definition is shown as follows:

$$z(t) = f(t) + i\hat{f}(t) = A(t)e^{i\theta(t)} \text{ when } \hat{f}(t) = \frac{1}{\pi}p\int_{-\infty}^{\infty}\frac{f(\tau)}{t-\tau}d\tau$$

Where z(t) is the echo signal in complex number form;
$A(t) = \sqrt{f^2(t) + \hat{f}^2(t)}$ is the envelope of echo signal, which is a function representing the energy intensity of echo signal;

$$\theta(t) = \tan^{-1}\frac{\hat{f}(t)}{f(t)}$$

is the instantaneous phase angle of echo signal, and the rewritten echo signal is shown as follows:

$$S_i(x,t) = A(x,t)(\cos(w_0(t)t(x)) + i\sin(w_0(t)t(x))) \quad (3)$$

$$S_t(x,t) = \quad (4)$$
$$A(x,t)(\cos(w_0(t)t(x) + w_0(t)\delta t(x)) + i\sin(w_0(t)t(x) + w_0(t)\delta t(x)))$$

According to the definition, the phase angle of equation (3) and equation (4) can be obtained, respectively:

$$\theta_i(x,t) = \tan^{-1}\left(\frac{\sin(w_0(t)t(x))}{\cos(w_0(t)t(x))}\right) = w_0(t)t(x)$$

$$\theta_t(x,t) = \tan^{-1}\left(\frac{\sin(w_0(t)t(x) + w_0(t)\delta t(x))}{\cos(w_0(t)t(x) + w_0(t)\delta t(x))}\right) = w_0(t)t(x) + w_0(t)\delta t(x)$$

According to the definition, the phase shift of time domain is equivalent to the instantaneous frequency shift of frequency domain. After the instantaneous phase angles $\theta_i$ and $\theta_t$ are differentiated with respect to time t for the first time, the clockwise angular frequencies $S_i(x,t)$ and $S_t(x,t)$ are obtained. After they are subtracted, $\delta t(x)$ is obtained as follows:

$$\frac{\partial}{\partial t}\theta_i(x,t) = w_0'(t)t(x) = 2\pi f_0 t(x) \quad (5)$$

$$\frac{\partial}{\partial t}\theta_t(x,t) = w_0'(t)t(x) + w_0'(t)\delta t(x) = 2\pi f_0 t(x) + 2\pi f_0 \delta t(x)$$

$$\frac{\partial}{\partial t}(\theta_t(x,t) - \theta_i(x,t)) = 2\pi f_0 \delta t(x)$$

$$\delta t(x) = \frac{1}{2\pi f_0} \cdot \frac{\partial}{\partial t}(\theta_t(x,t) - \theta_i(x,t))$$

Where $w_0(t) = 2\pi f_0 t$ and $f_0$ is the main frequency of ultrasound signal. After the instantaneous phase angle $\theta$ is partially differentiated for the first time, it will become the instantaneous angular frequency $\overline{w}$.

The previous assumption can be proved by equation (3), thus $\delta t(x)$ obtained from equation (3) can be substituted into equation (6):

$$\delta T(z) = \frac{c_0(z)}{2}\cdot\left(\frac{1}{\alpha(z) - \beta(z)}\right)\cdot\frac{\partial}{\partial z}\delta t(z) \quad (6)$$

The temperature $\delta T(x)$ can be obtained: $\quad (7)$ $$\delta T(x) = \frac{c_0}{2}\cdot\left(\frac{1}{\alpha(x) - \beta(x)}\right)\cdot\frac{1}{w_0'(x)}\cdot\frac{\partial}{\partial x}\frac{\partial}{\partial t}(\theta_t(x,t) - \theta_i(x,t))$$

$$\delta T(x) = \frac{c_0}{2}\cdot\left(\frac{1}{\alpha(x) - \beta(x)}\right)\cdot\frac{1}{w_0'(x)}\cdot\frac{\partial}{\partial x}\frac{\partial}{\partial t}(\theta_t(x,t) - \theta_i(x,t))$$

$$= \frac{c_0}{2}\cdot K \cdot \frac{1}{2\pi f_0}\cdot\frac{\partial}{\partial x}(\overline{w}_t(x) - \overline{w}_i(x))$$

From equation (7), it is obviously observed that the difference of current and initial instantaneous frequency is directly proportional to the temperature change. Therefore, unlike the prior art stating that the temperature can be estimated from the echo time-shift, it is also possible to measure the temperature change by detecting the instantaneous frequency.

One of the methods for estimating the local instantaneous frequency of a narrowband process is to measure the zero crossings of the radio-frequency (RF) signals. For a sinusoidal signal under a fixed sampling rate, the signal can be considered to be locally stationary, and the frequency can be simply regarded as the inverse of the period, or alternatively as half the inverse of the interval between the zero crossings as $$f_i \approx \frac{1}{2T_z}$$

where $T_z$ is the interval between the zero crossings that the zero crossings fall exactly on the sample points.

The advantage of using zero crossings to estimate the instantaneous frequency is that they are extremely simple computationally. However, their disadvantage is that they cannot be optimized, which may subject them to suboptimal conditions. Moreover, if the interval between the zero crossings is not an integer multiple of the samples, then quantization "noise" can be easily introduced in addition to linear averaging induced by the estimator. To reduce the variance in the zero-crossing-based instantaneous frequency estimation method, two approaches have been developed. First, we employ the estimator proposed according to which the average number of zero crossings within a time series with adjacent 2M points is taken as $$IF[n] \cong \frac{1}{2} \cdot \sum_{m=-M}^{M} |\text{sgn}[s(m)] - \text{sgn}[s(m-1)]| \cdot h(n-m)$$

where $$\text{sgn}[s(m)] = \begin{cases} 1, & \text{for } s(n) \geq 0 \\ -1, & \text{for } s(n) < 0 \end{cases}$$

and $$h[n-m] = \begin{cases} 1/2M, & \text{for } (n-m) \in [n-M, n+M] \\ 0, & \text{otherwize} \end{cases}$$

The selection of M introduces a bias-variance trade-off in the estimation. If M is large, and the IF law is nonlinear within the processing window, a bias will be introduced. On the other hand, if M is small, the bias is likely to be reduced but at the cost of higher variance. In our application, in order to emphasize the spatial resolution of local temperature changes, a small processing window of approximately half to one cycle of the sinusoidal signal was used, followed by signal smoothing by the introduction of low-pass filtering.

Secondly, a band-pass filter was introduced to reduce the noise caused by the discretized process.

$$\delta T(n) \approx k(n) \cdot [AF(n+1) - AF(n)]$$

where the constant term $C_0(n)/2 \cdot (1/(\alpha(n) - \beta(n)))$ was represented as $k(n)$, and $AF(n)$ denotes the accumulated instantaneous frequency form along the n time points with the addition of the low-pass filtering process Flow.

$$AF(n) = F_{low}\left[\sum_{n=1}^{N}(IF_2(n) - IF_1(n))\right]$$

The ultrasound radio frequency signal is the analysis result of the algorithm in equation (3). It has been proved that it is feasible to use the algorithm of equation (3) to estimate temperature. This mathematical temperature measuring algorithm for fast analyzing the ultrasound radio frequency (RF) can be used as non-invasive temperature inspection technique.

Figure 4:
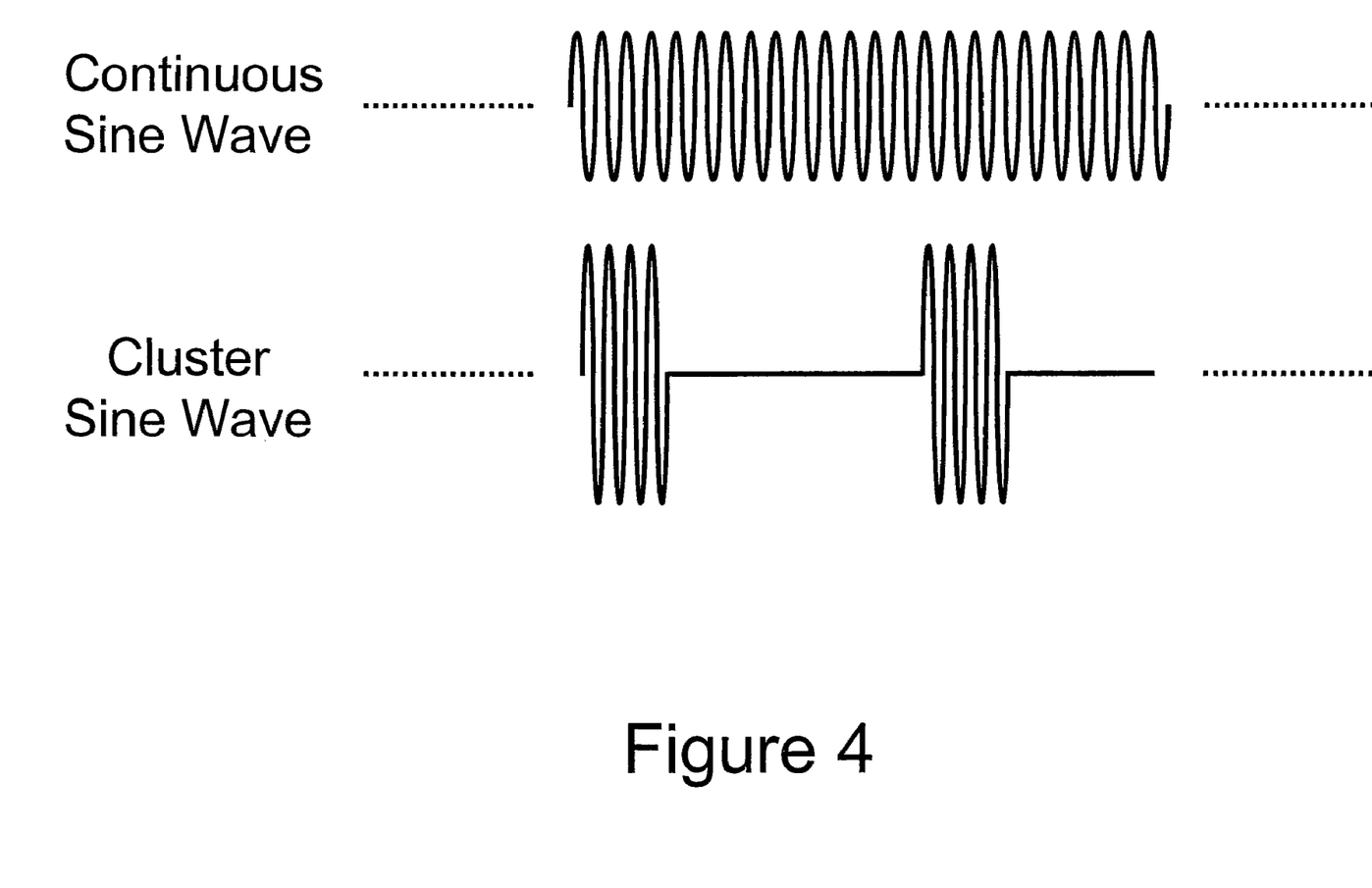
FIG. 4 is the diagram schematically illustrating the continuous sine wave and cluster wave of the invention.

As shown in FIG. 4, the invention uses a mechanism to avoid the interference of heating signal. The continuous sine wave is altered to the cluster sine wave. If the cluster wave is used instead of the heating signal, it will not need to switch the output of signal generator repeatedly. The time without any interference can be produced, which can be used by the ultrasound signal to measure the temperature. It can save the time of making command and instrument response. The design of cluster wave cycles can be used to reach the shortest suspension time, in order to show continuous heating feature of heating signal at macro aspect. Due to the heating signal is a continuous sine wave, it is necessary to switch the signal continuously to produce a measuring ultrasound signal environment without any interference. Upon switching, the delayed time will be accumulated by making command and instrument response.

Figure 5:
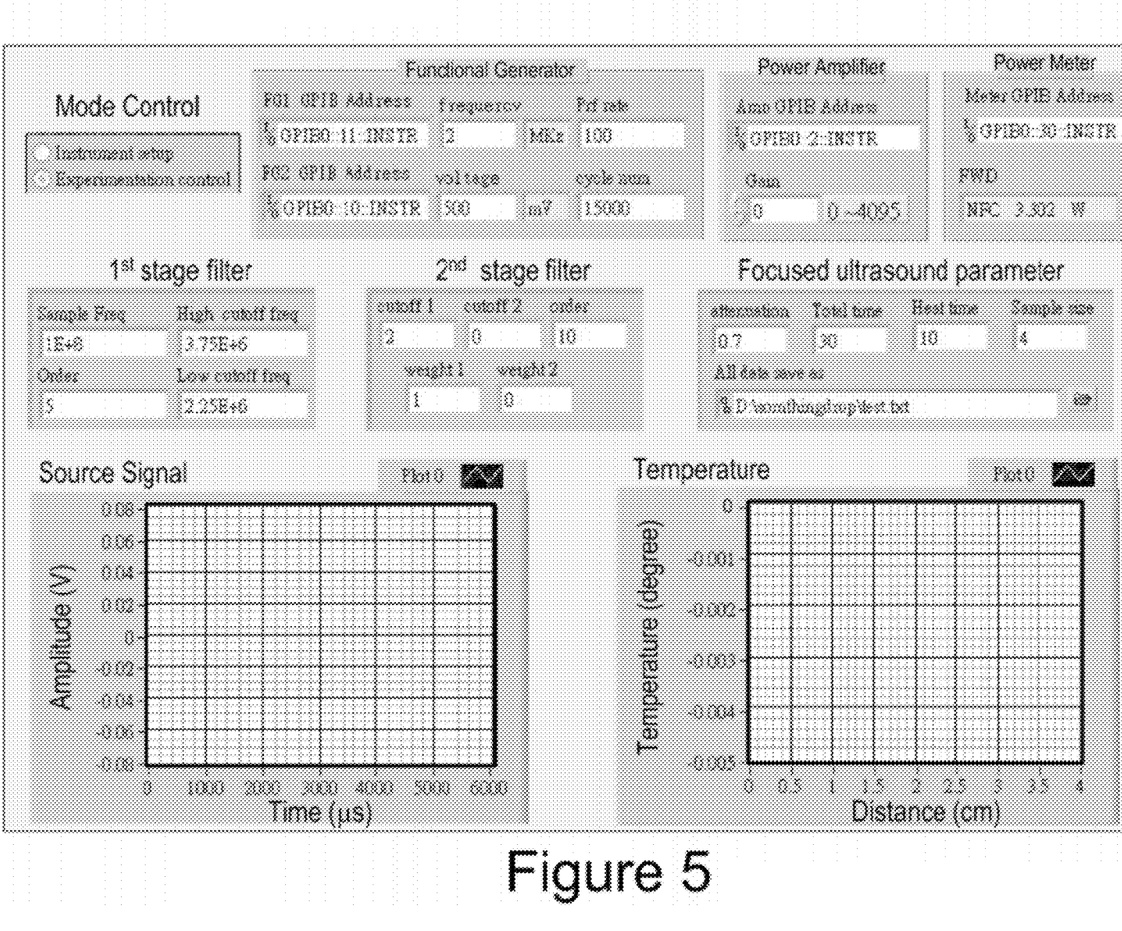
FIG. 5 is the diagram schematically illustrating the graphic operation interface of the invention.

In order to operate the system of the invention more easily, the Labview software can be used to create Graphics User Interface (GUI) control program. GUI is a kind of computer graphic interface. The user can see the graphic operation interface on the computer. FIG. 5 shows the graphic operation interface of the invention. Including:

(a) The heating system control: Comprising the frequency setup for the signal required to heat the probe, the amplifying times of radio frequency amplifier, and the output power monitoring of power detector, and the reaction in the interface.

(b) The experimental procedure control: This part is mainly to establish the experimental procedure, comprising the heating time, the temperature lowering time, tissue depth, data extraction speed and the storage position of the primitive ultrasound signal.

(c) Setup for the parameter of algorithm: According to different tissue characteristics and different central frequency of probe, different parameters are used in ultrasound temperature algorithm, comprising parameter of pre-filter, tissue attenuation coefficient, and parameter of post-filter etc.

(d) Result output: This part is to output the temperature distribution diagram instantaneously. The user can see the space distribution of temperature in the tissue, when the temperature is risen or lowered in the interface instantaneously.

Figure 6:
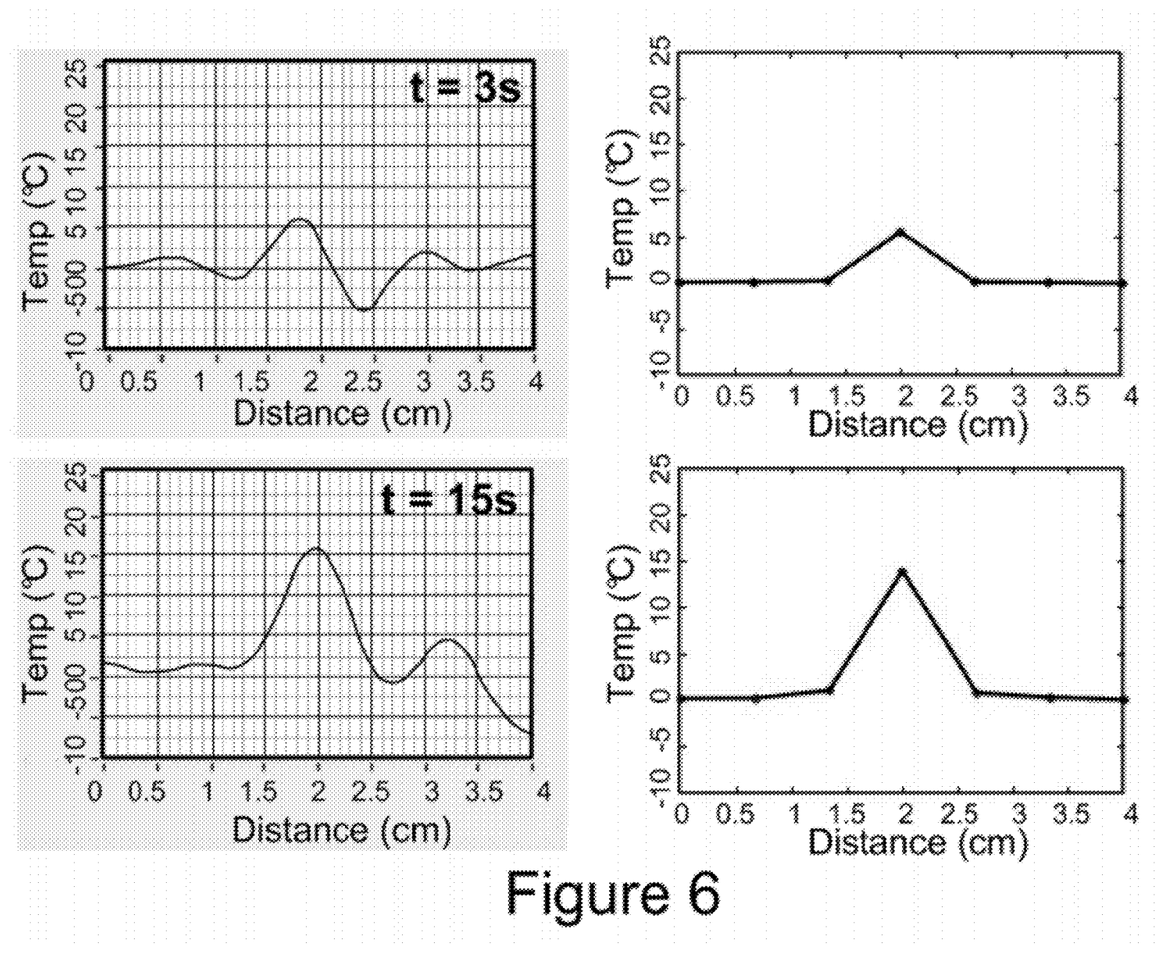
FIG. 6 shows the fragment picture extracted from the practical operation of the invention.
Figure 7:
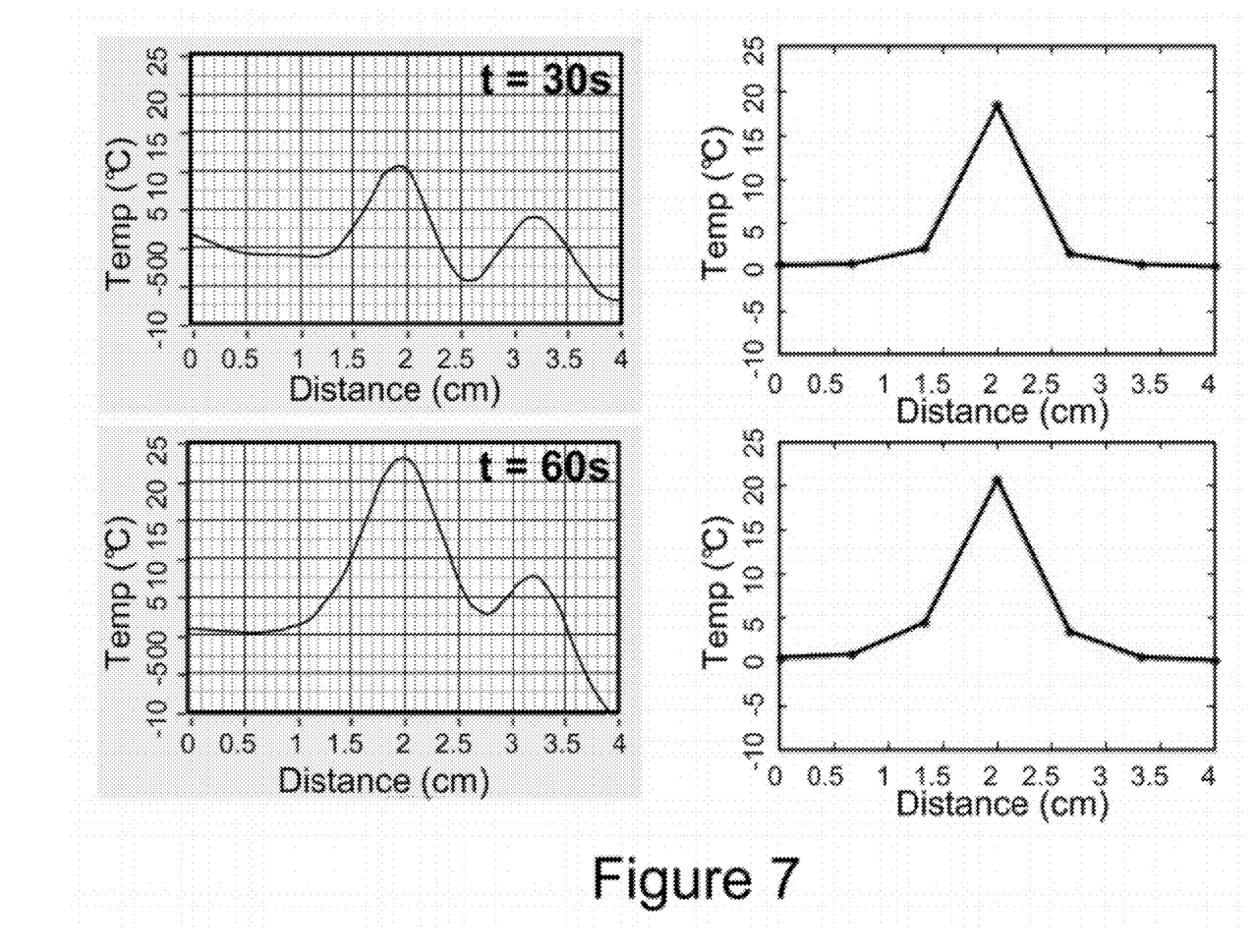
FIG. 7 shows the fragment picture extracted from the practical operation of the invention.

Refer to FIG. 6 and FIG. 7, the fragment picture extracted from the practical operation of the invention is shown. The result of real-time temperature estimation in the invention can be seen from the diagram. The single channel ultrasound probe is used as the measuring tool in the invention, so only one-dimensional temperature change can be obtained.

Figure 8:
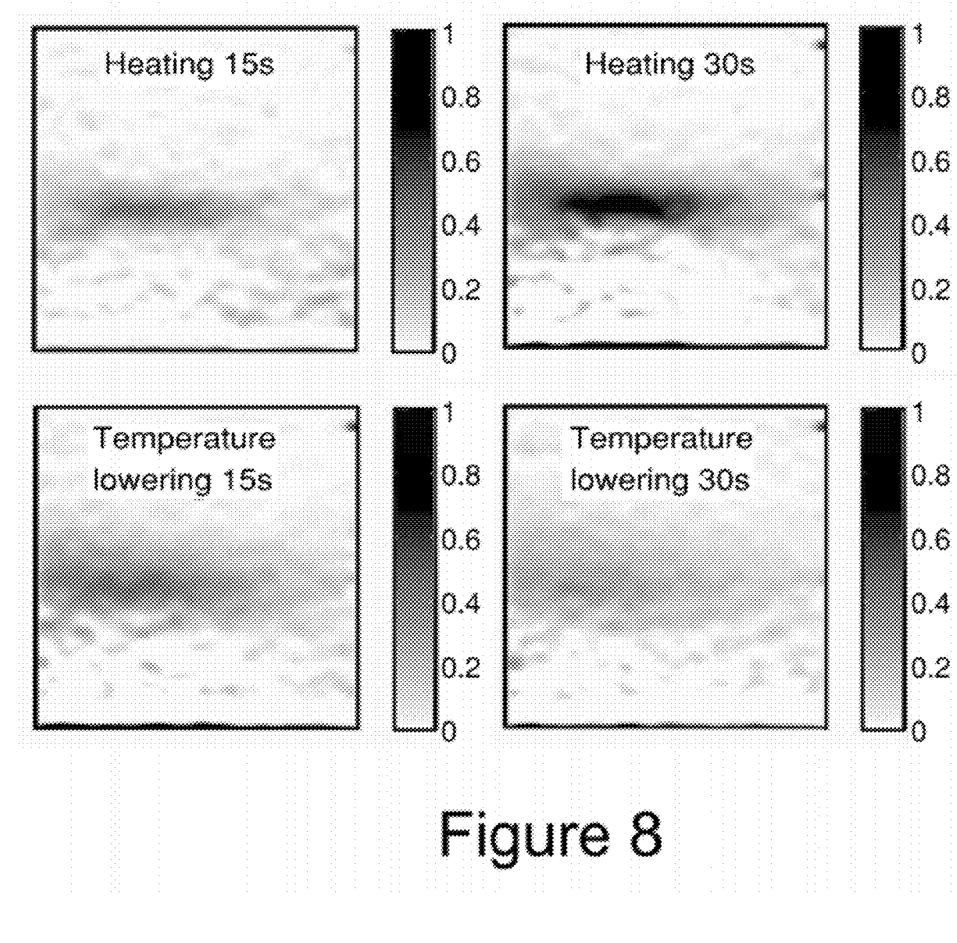
FIG. 8 shows the two-dimensional temperature distribution diagram.
Figure 9:
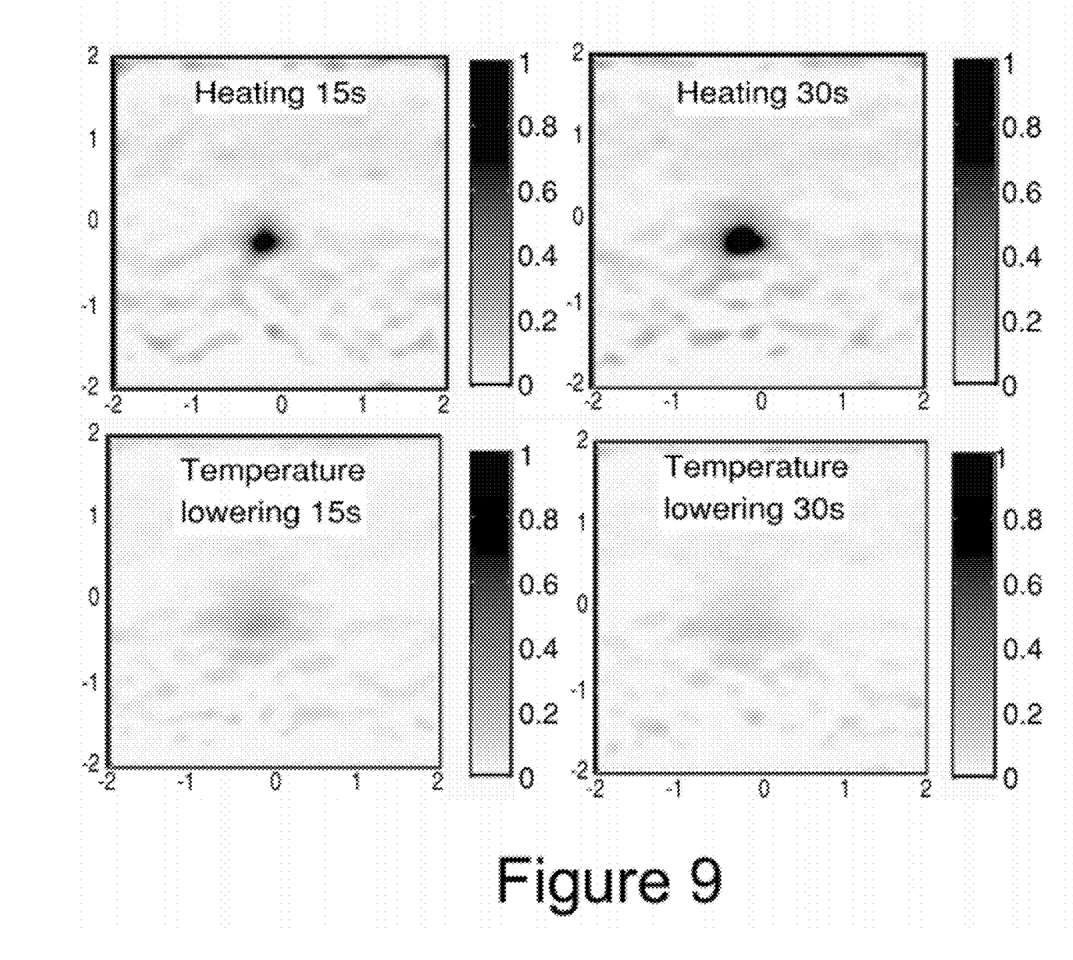
FIG. 9 shows the two-dimensional temperature distribution diagram.

Refer to FIG. 8 and FIG. 9, when the clinical multiple channel ultrasound probe is used as the measuring tool, the two-dimensional temperature distribution diagram can be obtained. From the figures, it can see the change of temperature rising after the heating is started, and the change of temperature lowering after the heating is ceased.

Figure 10:
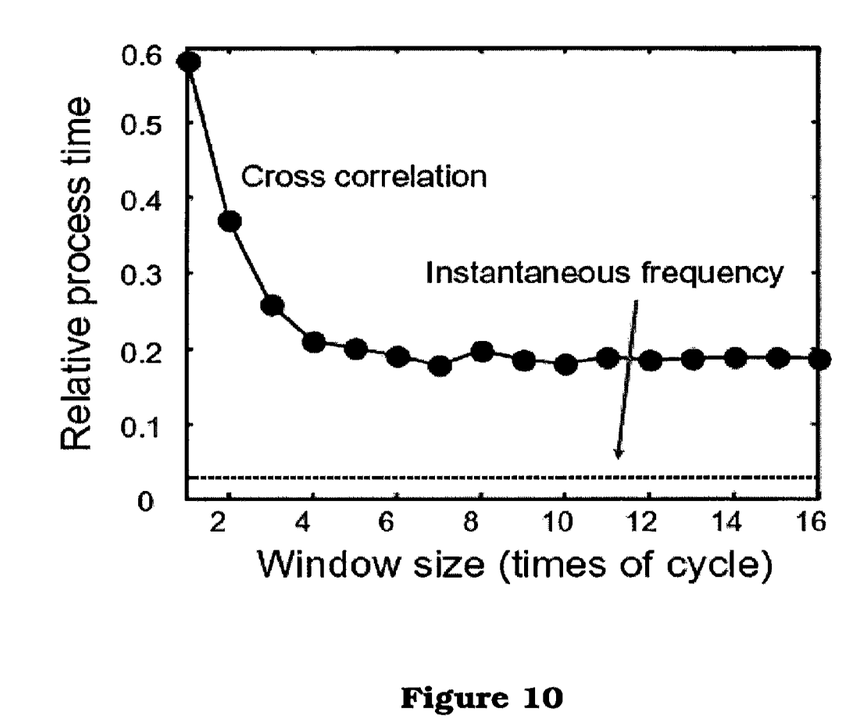
FIG. 10 shows a comparison of computational efficiencies between the proposed algorithm and cross-correlation-based temperature estimation algorithm.

FIG. 10 shows a comparison of computational efficiencies between the proposed algorithm and cross-correlation-based temperature estimation algorithm (window sizes ranged form $1\lambda$ to $16\lambda$). The results reveal that the instantaneous frequency algorithm contains almost six times better processing efficiency than that of the cross-correlation algorithm under the same resolution (i.e., a processing window size of $1\lambda$ was used in cross-correlation algorithm). Increasing the processing window size in cross-correlation algorithm can reduce the processing time since the total number of processing windows is reduced. However, the reduction in time obtained by increasing the processing window size gets saturated when the window size becomes greater than $6\lambda$, and the instantaneous-frequency-based algorithm still yields three times better processing efficiency than that obtained from the cross-correlation algorithm.

Figure 11:
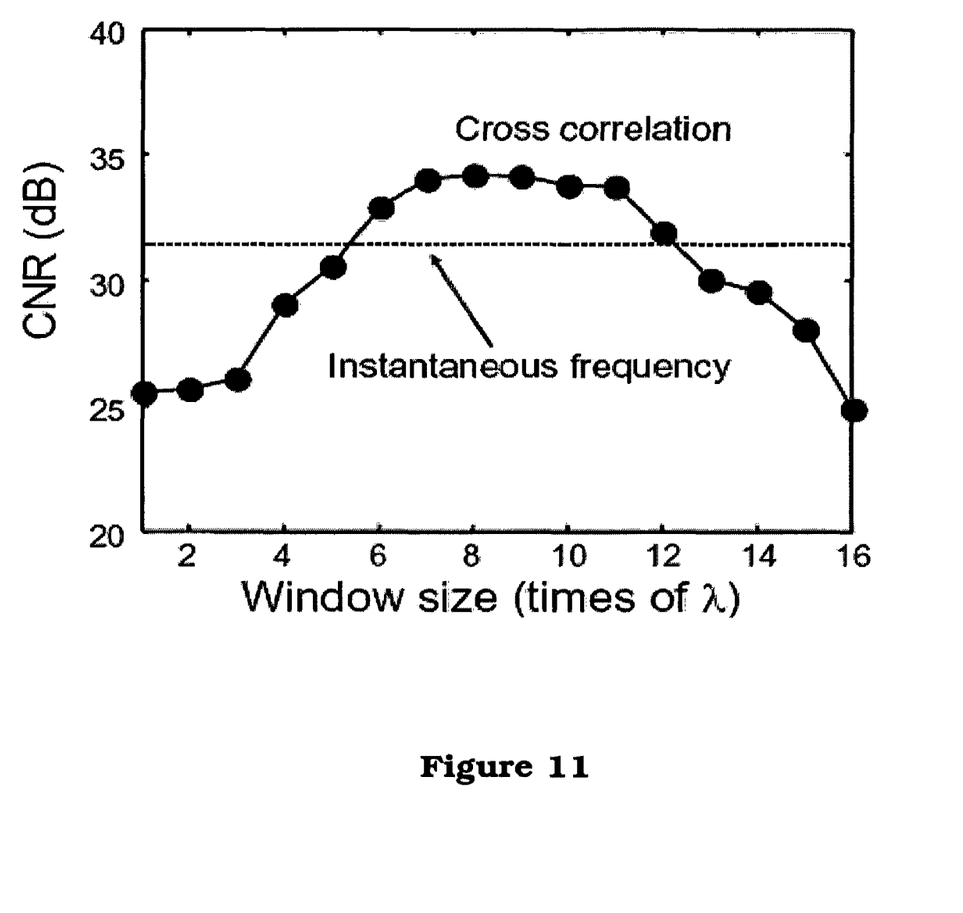
FIG. 11 shows the CNR values obtained from these two algorithms were compared and the results.

The Contrast-to-Noise Ratio (CNR) values obtained from these two algorithms were compared and the results are shown in FIG. 11. In the cross-correlation algorithm, a small processing window size induces high fluctuations outside the heat-up region and the CNR was relatively low. Processing window sizes ranging from 5λ to 8λ yield better noise rejection results than the proposed algorithm, and the CNR values can be increased by up to 37 dB. Longer processing window sizes did not provide further CNR improvements. In contrast, for the instantaneous-frequency-based algorithm, the CNR value is superior (32 dB) when the same processing window size is used as that in the cross-correlation algorithm (CNR of approximately 25 dB). When the results shown in FIG. 10 and FIG. 11 are compared, it can be shown that the proposed algorithm yields higher spatial resolution with superior processing efficiency, but the cross-correlation algorithm yields superior noise rejection when the processing window size is optimized with the trade-off between lower spatial resolution and inferior processing efficiency.

Figure 12:
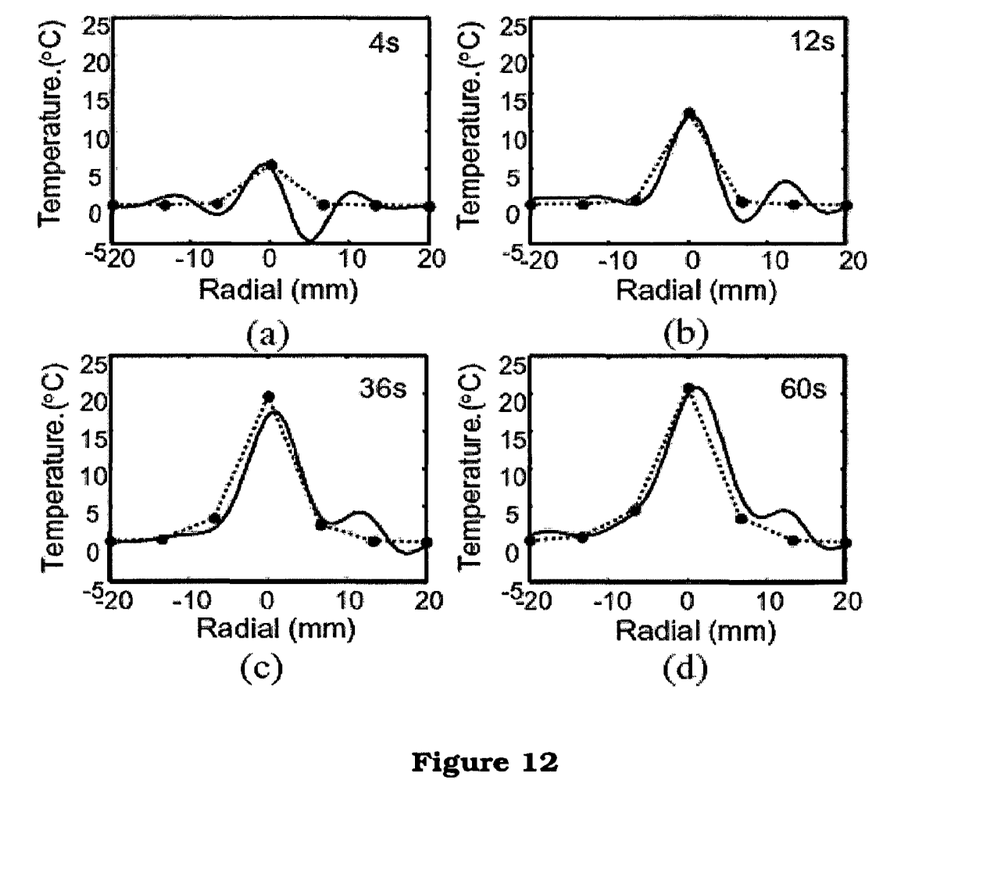
FIG. 12(a), 12(b), 12(c), 12(d) show the correlation between the calibrated temperature estimation as compared to the measured values.

FIG. 12($a$), 12($b$), 12($c$), 12($d$) show the correlation between the calibrated temperature estimation as compared to the measured values. Five thermocouples were placed diagonally to the RF pulse-echo lines. In this setting, the A-line passing through the focus along the radial direction was employed, and the tissue-mimicking phantoms were used for testing. An electrical power and sonication time of 50 W and 60 s were used, respectively. In these figures, only the data from the time points of 4, 12, 36, and 60 s are shown. The estimated echo-time shift was scaled to fit the measured temperature, and the scaling factor was assumed for later phantom or ex-vivo tissue use since the slope of (sound-speed)-to-temperature was very close among samples. The results reveal that after achieving adequate calibration, the estimated temperature elevation can have excellent correlation with the measured value. Further, it was revealed that good temperature prediction of up to 20° C. at the peak temperature value can be obtained in tissue-mimicking phantoms.

In the invention, the echo signal of ultrasound is analyzed to form the non-invasive tissue temperature measuring technique. The main principle is to use the echo signal of ultrasound formed by the attenuation of ultrasound signal with respect to temperature, and the speed change of ultrasound with respect to temperature.

According to the research, the absorption ability of big molecule on ultrasound energy will be reduced due to the rising of temperature; different echo signal will obtain different intensity of echo signal. Thus the analysis for the energy of echo signal can be used to estimate the temperature change. The transmitting speed of ultrasound is different under different temperature. The transmitting speed change of ultrasound in different transmission medium is also different upon temperature change.

For example, when the temperature of organ in human body is raised, the transmitting speed of ultrasound will be raised as will. However the body fat is opposite, the transmitting speed is decreased as the temperature is increased. Therefore the analysis method using the echo signal energy of ultrasound has to measure the small change of the echo signal energy. Thus it needs the analog/digital transformation with higher resolution, it is not easy to detect by the clinical ultrasound instrument. When the transmitting speed change of ultrasound is used to estimate the temperature, the requirement of hardware is much lower. Thus it is usually only to measure the phase shift between two echo signals of ultrasound, then the temperature change can be obtained.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A signal treatment method for an apparatus for real-time temperature measuring using a high-intensity focused ultrasound (HIFU) therapy system, comprising the steps:

activating the HIFU therapy system to heat tissue;

receiving a first echo signal of a reflected ultrasound wave from the heated tissue;

after a predetermined period of time, receiving a second echo signal of a reflected ultrasound wave from the heated tissue;

pre-filtering the echo signals to remove a first noise signal;

determining a current instantaneous angular frequency of the second filtered echo signal and an initial instantaneous angular frequency of the first filtered echo signal;

obtaining a phase shift signal between the first and second filtered echo signals using the change of instantaneous angular frequency between the initial instantaneous frequency of the first filtered echo signal and the current instantaneous frequency of the second filtered echo signal;

post-filtering the phase shift signal to remove a second noise signal; and obtaining a temperature value by taking the first mathematical derivative of the filtered phase shift signal.

2. An apparatus for real-time temperature measuring by using a high-intensity focused ultrasound (HIFU) therapy system, comprising:

an ultrasound burn module having a first signal generator, a power amplifier, a first ultrasound energy transferring device, and a computer comprising a non-transitory medium storing a temperature measuring algorithm, wherein execution of the temperature measuring algorithm by a computer processor causes the processor to execute a method for calculating a temperature change at a position of tissue using an ultrasound radio frequency signal, wherein the temperature measuring algorithm comprises:

$$S_i(x, t) = A(x, t)(\cos(w_0(t)t(x)) + i\sin(w_0(t)t(x))) \text{ and}$$

$$\delta T(x) = \frac{c_0}{2} \cdot K \cdot \frac{1}{2\pi f_0} \cdot \frac{\partial}{\partial x}(\overline{w}_t(x) - \overline{w}_i(x)) \text{ algorithms,}$$

wherein $\delta T(x)$ is a temperature change at position x, $S_i(x, t)$ is the received one-dimensional spatial and temporal dependent radio-frequency ultrasound echo signal at position x and at time t, $A(x, t)$ is the amplitude of $S_i(x, t)$ when expressing in a complex form, $t(x)$ is a received echo-signal time that may contain small local time-shift caused by local temperature change, $w_0 = 2\pi f_0$ is a center angular frequency of ultrasound signal, $c_0 \cdot K/2$ is a constant term, and $\overline{w}(x)$ is an instantaneous angular frequency at position x for showing a difference of a current instantaneous frequency $\overline{w}_t(x)$ and an initial instantaneous frequency $\overline{w}_i(x)$ being directly proportional to a temperature change at position x;

a real-time temperature monitoring module having a pre-filter and a post-filter;

an ultrasound signal interference module having the first signal generator, a second signal generator, a pulse generator/receiver and a second ultrasound energy transferring device; and a Graphics User Interface for displaying the real-time temperature measurements.

3. A computer program product comprising a non-transitory computer readable medium storing a temperature measuring executable software using an ultrasound radio frequency signal, wherein execution of the executable software by a processor causes the processor to execute a method for calculating a temperature change at a position of tissue, the software comprising:

$$S_i(x, t) = A(x, t)(\cos(w_0(t)t(x)) + i\sin(w_0(t)t(x))) \text{ and}$$

$$\delta T(x) = \frac{c_0}{2} \cdot K \cdot \frac{1}{2\pi f_0} \cdot \frac{\partial}{\partial x}(\overline{w}_t(x) - \overline{w}_i(x)) \text{ algorithms,}$$

wherein $\delta T(x)$ is a temperature change at position x, $S_i(x, t)$ is the received one-dimensional spatial and temporal dependent radio-frequency ultrasound echo signal at position x and at time t, $A(x, t)$ is the amplitude of $S_i(x, t)$ when expressing in a complex form, $t(x)$ is a received echo-signal time that may contain small local time-shift caused by local temperature change, $w_0 = 2\pi f_0$ is a center angular frequency of ultrasound signal, $c_0 \cdot K/2$ is a constant term, and $\overline{w}(x)$ is an instantaneous angular frequency at position x for showing a difference of a current instantaneous frequency $\overline{w}_t(x)$ and an initial instantaneous frequency $\overline{w}_i(x)$ being directly proportional to a temperature change at position x.

* * * * *